United States Patent [19]

Schaar

[11] 4,209,016
[45] Jun. 24, 1980

[54] DIAPER WITH ELASTIC FASTENER

[75] Inventor: Charles H. Schaar, Lake Zurich, Ill.

[73] Assignee: Colgate-Palmolive Company, New York, N.Y.

[21] Appl. No.: 883,446

[22] Filed: Mar. 6, 1978

Related U.S. Application Data

[60] Continuation-in-part of Ser. No. 836,162, Sep. 23, 1977, Pat. No. 4,090,516, which is a division of Ser. No. 756,309, Jan. 3, 1977, Pat. No. 4,074,716.

[51] Int. Cl.² .............................................. A61F 13/16
[52] U.S. Cl. ............................. 128/287; 128/DIG. 30
[58] Field of Search ................ 128/284, 287, DIG. 30

[56] References Cited

U.S. PATENT DOCUMENTS

| | | | |
|---|---|---|---|
| 3,920,018 | 11/1975 | Schaar | 128/287 |
| 3,950,824 | 4/1976 | Karami | 128/287 UX |
| 3,967,622 | 7/1976 | Cepuritis | 128/287 |
| 3,983,876 | 10/1976 | Cepuritis | 128/287 |
| 3,990,449 | 11/1976 | Cheslow | 128/287 |
| 3,995,639 | 12/1976 | Cheslow | 128/287 |
| 4,002,172 | 1/1977 | Feldman | 128/284 |
| 4,010,754 | 3/1977 | Pieniak | 128/287 |
| 4,074,716 | 2/1978 | Schaar | 128/287 |

*Primary Examiner*—Robert W. Michell
*Assistant Examiner*—C. W. Shedd
*Attorney, Agent, or Firm*—Powell L. Sprunger

[57] ABSTRACT

A disposable diaper comprising, an absorbent pad assembly having opposed surfaces, a pair of side edges, and a pair of end edges connecting the side edges. The diaper has a tape fastener comprising, tape means having a first portion secured to one of the surfaces of the pad assembly, a split securement portion for attachment to a spaced portion of the diaper and distribution of forces in the fastener.

3 Claims, 18 Drawing Figures

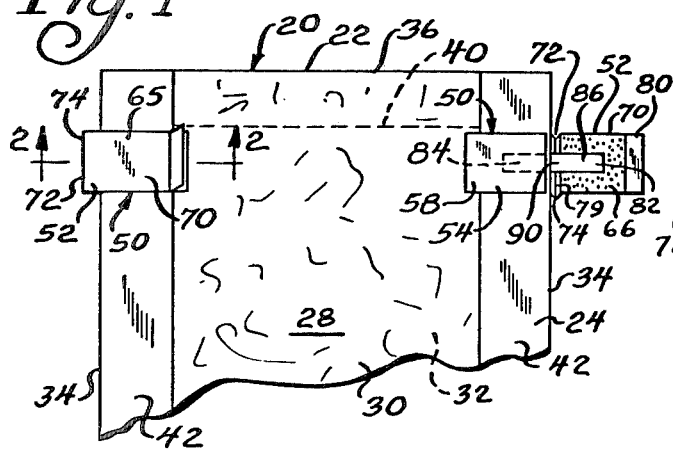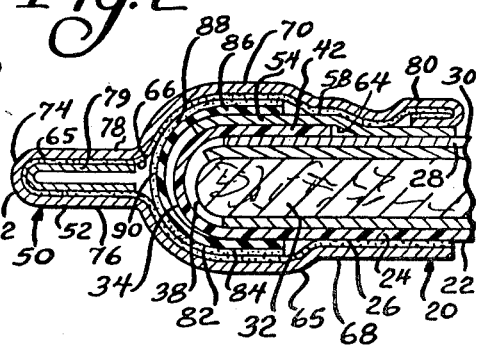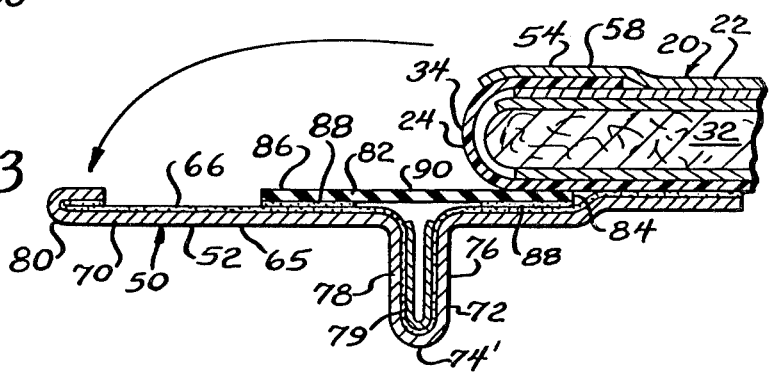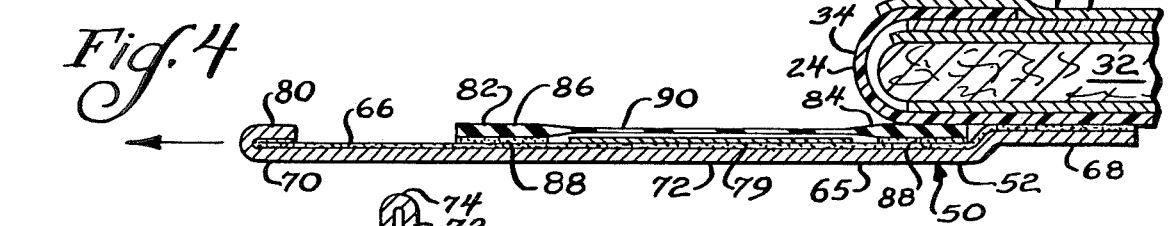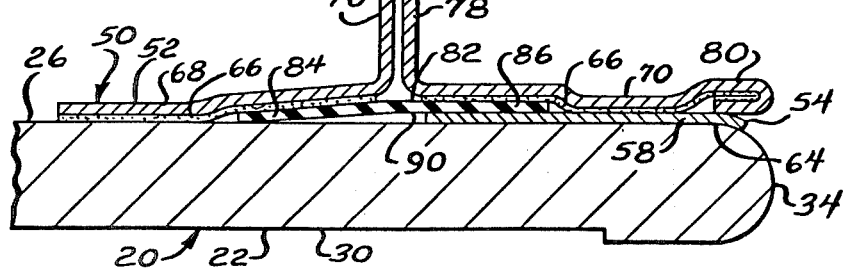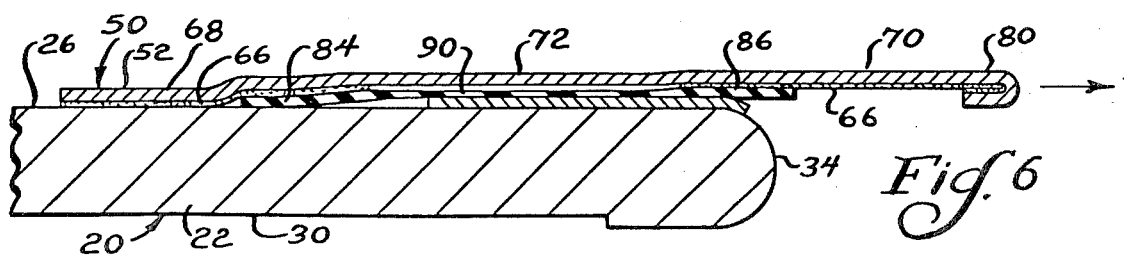

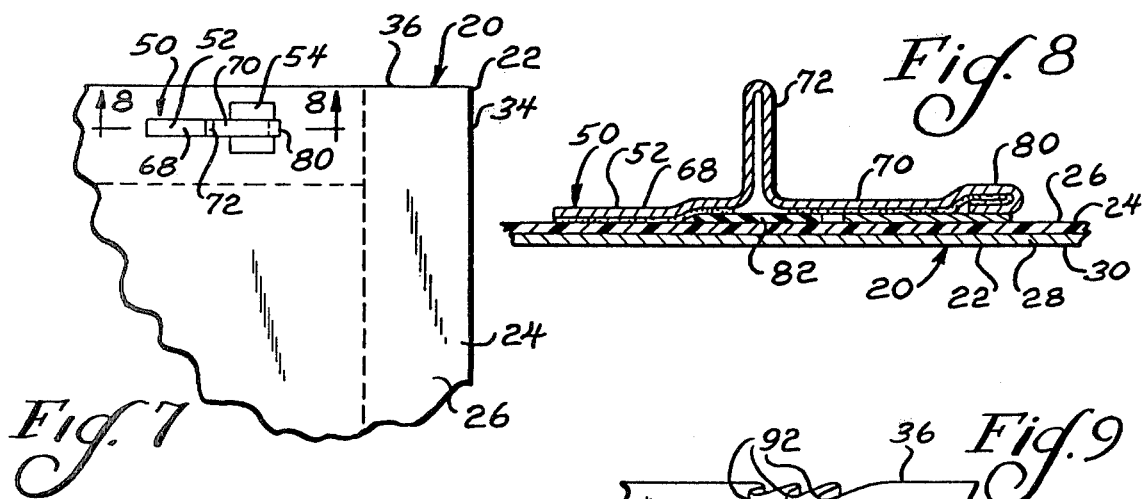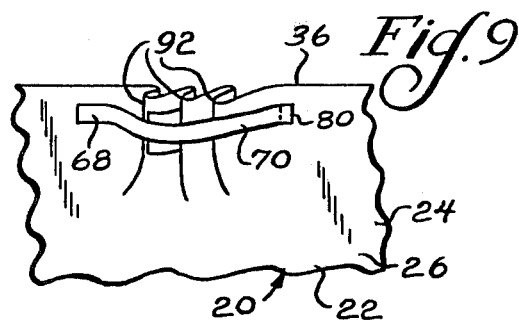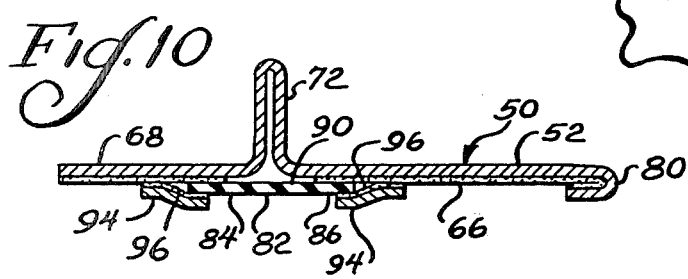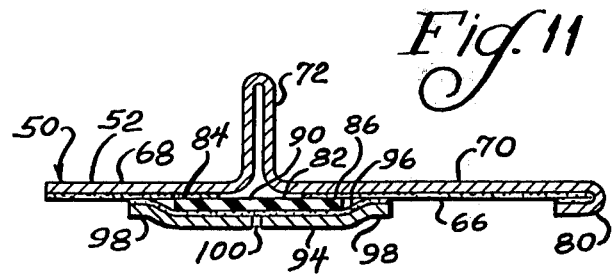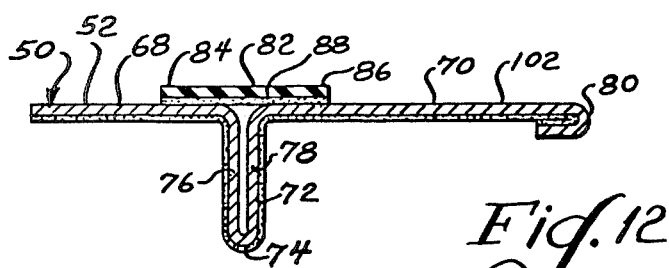

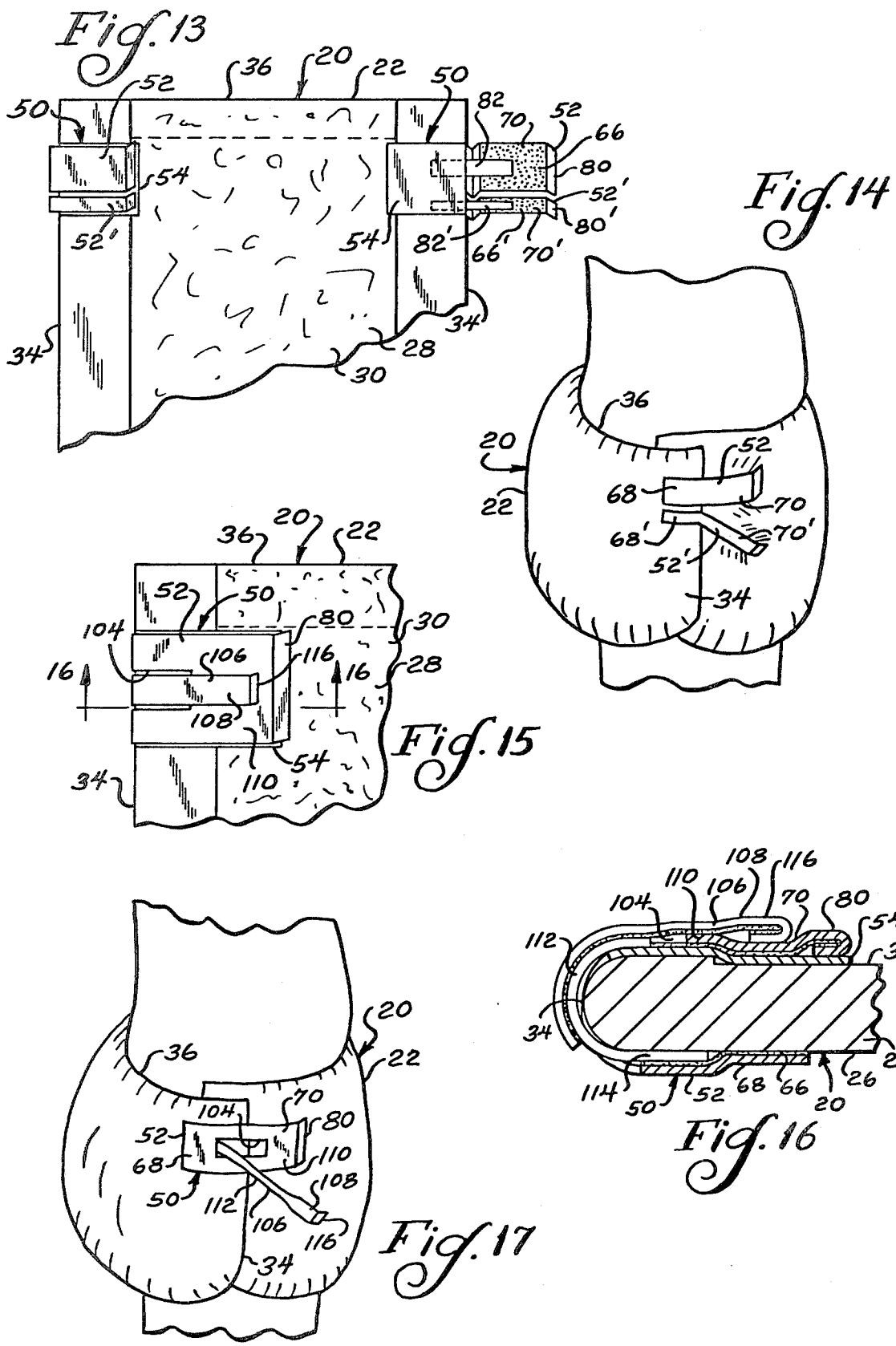

DIAPER WITH ELASTIC FASTENER

BACKGROUND OF THE INVENTION

This application is a continuation-in-part of application Ser. No. 836,162, filed Sept. 23, 1977, now U.S. Pat. No. 4,090,516, a divisional of application Ser. No. 756,309, filed Jan. 3, 1977, now U.S. Pat. No. 4,074,716.

The present invention relates to absorbent articles, and more particularly to disposable diapers.

A various assortment of disposable diapers have been proposed for use on infants, and have become increasingly popular with parents since they may be discarded after a single use and need not be laundered. Such diapers are normally constructed having a fluid impervious backing sheet, a fluid pervious top or cover sheet, and an absorbent pad intermediate the backing and cover sheets.

Many of the diapers have been provided with tape fasteners which are used to secure the diaper about the infant. Such fasteners generally take the form of a pessure-sensitive tape strip having a first end attached to the diaper and a second securement end which is attached to the diaper during placement. Prior to use, adhesive on the securement end is covered to prevent premature contact of the adhesive against the diaper or other article.

An overriding consideration in construction of the diaper is the cost of manufacture and the diaper materials, since the diaper must be inexpensive to the consumer due to its disposability. Accordingly, the backing sheets of such diapers have been made from a relatively thin plastic material, such as polyethylene, in order to reduce the cost of the backing sheet and the diaper. However, it has been found that when forces are applied to the tape strip during placement and use of the diaper, the tape strips have a tendency to tear the backing sheet and become ruptured from the diaper, thus rendering the diaper relatively useless. Additionally, it is desired that the tape fastener provides a snug fit and prevents a loose fit of the diaper about the infant.

SUMMARY OF THE INVENTION

A principal feature of the present invention is the provision of a disposable diaper having an improved tape fastener.

The diaper of the present invention comprises, an absorbent pad assembly having opposed surfaces, a pair of side edges, and a pair of end edges connecting the side edges. The diaper has a tape fastener comprising, tape means having a first portion secured to one of the surfaces of the pad assembly, a split securement portion for attachment to a spaced portion of the diaper.

A feature of the present invention is that the securement portion may be spread during placement of the diaper.

Thus, a feature of the invention is that the fastener distributes forces in the placed diaper.

Another feature of the invention is that the fastener minimizes the possibility that the securement portion may rupture from the diaper backing sheet.

Still another feature of the invention is that the spread securement portion provides a snug fit of the diaper about the infant.

Further features will become more fully apparent in the following descrliption of the embodiments of this invention and from the appended claims.

DESCRIPTION OF THE DRAWINGS

In the drawings:

FIG. 1 is a fragmentary front plan view of a disposable diaper having a tape fastener of the present invention;

FIG. 2 is a fragmentary sectional view taken substantially as indicated along the line 2—2 of FIG. 1;

FIG. 3 is a fragmentary sectional view of the diaper of FIG. 2 showing the tape fastener in an unfolded configuration preparatory to use;

FIG. 4 is a fragmentary sectional view of the diaper of FIG. 3 showing the tape fastener in an extended configuration;

FIG. 5 is a fragmentary sectional view of the diaper showing another embodiment of the tape fastener of the present invention;

FIG. 6 is a fragmentary sectional view of the diaper of FIG. 5 showing the tape fastener in an extended configuration;

FIG. 7 is a fragmentary back plan view of a diaper showing another embodiment of a tape fastener of the present invention;

FIG. 8 is a fragmentary sectional view taken substantially as indicated along the line 8—8 of FIG. 7;

FIG. 9 is a fragmentary back plan view showing the fastener of FIG. 7 in an extended configuration during use;

FIG. 10 is a sectional view of another embodiment of the fastener of the present invention;

FIG. 11 is a sectional view of another embodiment of the fastener of the present invention;

FIG. 12 is a sectional view of another embodiment of the fastener of the present invention;

FIG. 13 is a fragmentary front plan view of a diaper having another embodiment of the fastener of the present invention;

FIG. 14 is an elevational view showing the fastener of FIG. 13 in an extended configuration during use;

FIG. 15 is a fragmentary front plan view of a diaper showing another embodiment of the fastener of the present invention;

FIG. 16 is a sectional view taken substantially as indicated along the line 16—16 of FIG. 15;

FIG. 17 is an elevational view showing the fastener of FIG. 15 attached to a remote portion of the diaper durng use.

DESCRIPTION OF THE PREFERRED EMBODIMENTS

Figure 18:
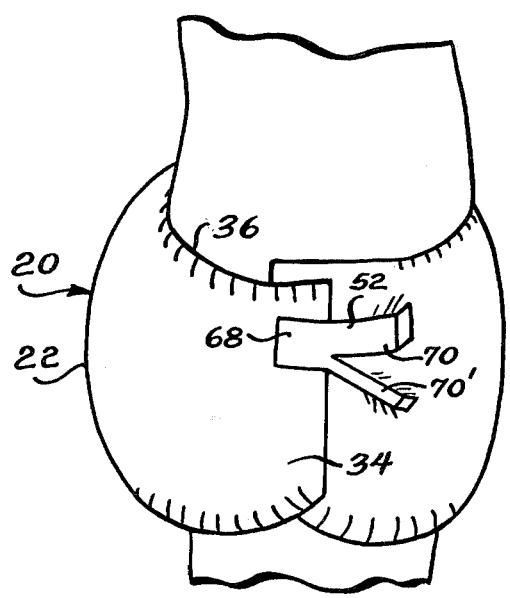
FIG. 18 is an elevational view showing an embodiment of the fastener of the present invention.

Referring now to FIGS. 1 and 2, there is shown a disposable diaper generally designated 20 having an absorbent pad assembly 22. The pad assembly 22 has a fluid impervious backing sheet 24, such as polyethylene, defining a back surface 26 of the pad assembly, a fluid pervious cover or top sheet 28, such as a nonwoven material, defining a front surface 30 of the pad assembly 22, and an absorbent pad 32, such as comminuted wool pulp termed in the art as fluff, located intermediate the backing sheet 24 and cover sheet 28. The pad assembly 22 has a pair of side edges 34, and a pair of end edges 36 connecting the side edges 34. The absorbent pad 32 also has a pair of side edges 38 and end edges 40 connecting the side edges 38. In a preferred form, as shown, the side edges 38 of the pad 32 are located adjacent the side edges 34 of the pad assembly 22, and the fluid impervious backing sheet 24 has lateral side margins 42 folded over and secured to the top sheet 28, such that the backing sheet side margins 42 cover lateral side margins of the absorbent pad 32.

The diaper has a pair of tape fasteners generally designated 50 having a pressure-sensitive tape strip 52 and a release sheet 54, with each of the fasteners being located adjacent a side edge 34 of the pad assembly 22. The release sheets 54 have an outer release surface 58 and are attached to the front surface 30 of the pad assembly 22 adjacent the side edges 34 by suitable means, such as adhesive 64. The release sheet 54 may be made from any suitable material, such as paper or polyethylene, and the outer release surface 58 of the paper release sheet may be formed by a suitable silicone treatment or coating.

The tape strip 52 has a relatively inextensible backing 65, such as paper, adhesive 66 on a front surface of the backing 65, a first end portion 68 secured to the back surface 26 of the pad assembly by the adhesive 66 adjacent the side edge 34, a securement end portion 70 reto the diaper backing sheet 24, thus minimizing the possibility that the backing sheet may be torn and tape strip may be ruptured from the diaper. At the same time, the elastic band 82 constrains expansion of the extensible portion 72, and causes a close fit of the diaper about the infant. In addition, with reference to FIG. 4, the extensible portion 72 limits the amount of longitudinal expansion of the tape strip 52 and elastic strip 82, and prevents overextension of the tape strip which otherwise might cause a loose fitment of the diaper about the infant.

Another embodiment of the tape fastener is illustrated in FIGS. 5 and 6, in which like reference numerals designate like parts. In this embodiment, the release sheet 54 is attached to the back surface 26 of the pad assembly 22 adjacent the side edge 34, and the first portion 68 of the tape strip 52 is spaced from the side edge 34 and located adjacent the release sheet 54. As before, the eleastic strip 82 is connected between the first and securement portions 68 and 70, and the adhesive 66 on the securement portion 70 is releasably atends 98 attached by adhesive 96 to the adhesive 66 on the tape strip 52. The anchoring strip 94 has a slit 100 separating end portions of the anchoring strip 94 intermediate the ends 84 and 86 of the elastic strip 82 to permit expansion of the elastic strip 82.

Another embodiment of the present invention is illustrated in FIG. 12, in which like reference numerals designate like parts. In this embodiment, back surfaces 102 of the strip first and second sections 76 and 78 face each other in the folded extensible portion 72, and the elastic strip 82 is secured to the back surface 102 of the first and securement portions 68 and 70. The extensible portion 72 permits expansion of the tape strip 52 while the elastic strip 82 constrains longitudinal extension of the tape strip 52.

Another embodiment of the present invention is illustrated in FIGS. 13 and 14, in which like reference numerals designate like parts. In this embodiment, the diaper fastener has a pair of tape strips 52 and 52' on each of the diaper sides, with each of the tape strips 52 and 52' being similar to the fastener described in connection with FIGS. 1-4. As shown, the tape strip 52' is relatively narrow and the tape strip 52 is located intermediate the second tape strip 52' and the end edge 36 of the pad assembly 22. Also, the securement portions 70 and 70' of both tape strips 52 and 52' may be releasably attached to a common release sheet 54. In use, the securement portions 70 and 70' are peeled from the release sheet 54, and the larger tape strip 52 is utilized to secure the diaper about an infant, as shown in FIG. 14. Next, the second tape strip 52' may be attached to a lower spaced portion of the diaper in order to apply tension to this diaper portion after attachment, and secure a snug fit of the lower diaper portion about the infant.

Another embodiment of the present invention is illustrated in FIGS. 15-17, in which like reference numerals designate like parts. In this embodiment, the primary tape strip 52 has a first portion 68 attached to the back surface 26 of the pad assembly 22, and the securement portion 70 is releasably attached to a release sheet 54 on the front surface 30 of the pad assembly 22. As shown, the tape strip 52 has a cut-out 104 adjacent the side edge 34 of the pad assembly, and an auxiliary strip 106 extends through the cut-out 104. The auxiliary strip 104 has an adhesive-bearing securement portion 108 releasably attached to a back release surface 110 of the tape strip securement portion 70, and an elastic strip 112 extending between the securement portion 108 and the pad assembly where an end 114 of elastic strip 112 is secured to the diaper beneath the first strip portion 68. In use, the securement portion 70 of the tape strip 52 is utilized to secure the diaper about an infant, as shown in FIG. 17. Next, a tab 116 on the auxiliary strip 106 is utilized to peel the securement portion 108 from the tape strip 52, and the securement portion 108 of the auxiliary strip 106 is attached to a lower spaced portion of the diaper. Thus, the elastic strip 112 of the auxiliary strip 106 causes tension on the lower part of the diaper to obtain a snug fit of this diaper part about the infant.

Another embodiment of the present invention is illustrated in FIG. 18, in which like reference numerals designate like parts. In this embodiment, the diaper has a pair of tape fasteners adjacent opposed side edges 34 of the pad assembly 22, as previously described. Each tape fastener has a tape strip 52 having a first end portion 68 attached by adhesive to the back surface of the backing sheet adjacent the associated side edge 34, such that the first end portion 68 defines a fixed end of the tape strip. The tape strip also has a severance line in an outer portion forming spread securement portions 70 and 70' which define a free working end of the tape strip. As shown, the severance line may extend from an outer edge of the tape strip to a location adjacent the side edge 34, such that the securement portions 70 and 70' may be spread and attached at spaced locations in a remote portion of the diaper during placement. In this configuration, the securement portions 70 and 70' form anchoring legs which diverge from the side edge 34 of the pad assembly 22 toward the outer edge of the tape strip 52. The spread securement portions 70 and 70' of the tape strip 52 thus distribute forces in the fastener and minimize the possibility that the securement portion or working end of the fastener may rupture the backing sheet on the remote portion of the diaper. In addition, the securement portion 70' may be attached to a lower spaced portion of the diaper in order to apply tension to this diaper portion after attachment, and secure a snug fit of the lower diaper portion about the infant. As previously discussed in connection with FIGS. 13 and 14, the securement portions 70 and 70' may be releasably attached to a common release sheet on the front of the diaper, and each may have folds and elastic members, if desired.

The foregoing detailed description is given for clearness of understanding only, and no unnecessary limitations should be understood therefrom, as modifications will be obvious to those skilled in the art.

I claim:

1. A disposable diaper, comprising:
   an absorbent pad assembly having first and second opposed waistline portions, opposed surfaces, a pair of opposed side edges, and a pair of end edges connecting the side edges; and
   a pair of elongated rectangular tape fasteners comprising a pair of integral pressure-sensitive tape strips having first end portions defining fixed ends of the tape strips secured to one of said surfaces of the pad assembly of the first waistline portion adjacent the opposed side edges thereof, second end portions defining free working ends of the tape strips having free split securement portions for attachment to remote surface portions of the second waistline portion, with said second end portions including uninterrupted severance lines extending longitudinally through said rectangular fasteners from an outer edge of the tape strip to a location adjacent said side edges of the pad assembly and defining said split securement portions on opposed sides of said severance lines, said split securement portions being spreadable so as to be spaced from each other when attached to said second waistline portion and thereby distribute the securing forces in the fastener over a wide area of the diaper surface portions and secure a snug fit of the diaper on an infant, and release means releasably attached to and covering adhesive on all said securement portions.

2. The diaper of claim 1 wherein said first end portions are attached to a back surface of the pad assembly, and said release means is located on an opposed front surface of the pad assembly adjacent said one side edge.

3. The diaper of claim 2 wherein said release means comprises a common release sheet for said securement portions attached to the front surface of the pad assembly.

* * * * *